United States Patent

Cain et al.

[11] Patent Number: 6,159,523
[45] Date of Patent: *Dec. 12, 2000

[54] COMPOSITION BASED ON FISH OIL

[75] Inventors: Frederick William Cain, Wormerveer, Netherlands; Stephen Raymond Moore; Gerald Patrick McNeill, both of Sharnbrook, United Kingdom

[73] Assignee: Loders-Croklaan BV, Wormerveer, Netherlands

[ * ] Notice: This patent is subject to a terminal disclaimer.

[21] Appl. No.: 09/457,307

[22] Filed: Dec. 9, 1999

Related U.S. Application Data

[63] Continuation of application No. 09/077,200, May 26, 1998, Pat. No. 6,020,020.

[30] Foreign Application Priority Data

Nov. 24, 1995 [EP] European Pat. Off. .............. 95308456

[51] Int. Cl.$^7$ ...................................................... A23D 9/00
[52] U.S. Cl. ........................... 426/601; 426/601; 426/33; 426/55; 426/417; 554/8; 554/18; 554/174; 554/175; 554/160; 435/134; 435/271; 424/523
[58] Field of Search ..................................... 426/601, 602, 426/33, 55, 417; 554/18, 174, 175, 160; 424/523; 435/134, 271

[56] References Cited

U.S. PATENT DOCUMENTS

| | | | |
|---|---|---|---|
| 4,675,132 | 6/1987 | Stout et al. ............................. | 554/174 |
| 4,764,392 | 8/1988 | Yasufuku ................................ | 426/603 |
| 4,792,418 | 12/1988 | Rubin et al. ........................... | 554/186 |
| 4,874,629 | 10/1989 | Chang et al. ........................... | 426/601 |
| 4,913,921 | 4/1990 | Schroeder ............................... | 426/541 |
| 4,966,734 | 10/1990 | Hoercher et al. ....................... | 554/190 |
| 5,006,281 | 4/1991 | Rubin .................................... | 424/522 |
| 5,130,061 | 7/1992 | Cornieri et al. ........................ | 554/167 |
| 5,149,851 | 9/1992 | Stout et al. ............................. | 554/165 |
| 5,151,291 | 9/1992 | Tokaeren ................................ | 426/581 |
| 5,397,778 | 3/1995 | Forse ..................................... | 426/804 |
| 5,434,183 | 7/1995 | Larsson-Backstrom ................. | 514/549 |
| 5,444,054 | 8/1995 | Garleb ................................... | 514/54 |
| 5,502,077 | 3/1996 | Breivik et al. .......................... | 514/560 |
| 5,532,002 | 7/1996 | Story ..................................... | 424/456 |
| 5,639,474 | 6/1997 | Woo ...................................... | 424/452 |
| 5,679,809 | 10/1997 | Bertoli et al. .......................... | 554/186 |
| 5,686,131 | 11/1997 | Sato ...................................... | 426/606 |
| 5,693,835 | 12/1997 | Konishi et al. ......................... | 554/141 |
| 5,698,594 | 12/1997 | Breivik et al. .......................... | 514/560 |
| 5,714,472 | 2/1998 | Gray ..................................... | 426/72 |
| 5,738,871 | 4/1998 | Story ..................................... | 424/451 |
| 5,756,143 | 5/1998 | Cain ...................................... | 426/606 |
| 5,840,945 | 11/1998 | Tsujiwaki .............................. | 554/192 |
| 6,020,020 | 2/2000 | Cain ...................................... | 426/601 |

FOREIGN PATENT DOCUMENTS 2241503  4/1991  United Kingdom .

OTHER PUBLICATIONS

Tanaka 1994 J. Am. Oil Chem Soc. vol. 71 (3) 331–334.
Derwent Acc. 1986–064833 JP 61015650.
Shimada 1994 J Am Oil Chem Soc vol. 71 (9) 951–954.
Derwent Acc 1995–093761 JP 07017860.
Lee 1992 Intl J. of Food Science & Tech 27: 73–76.
Derwent Acc No. 1995–310360 US 5444054.
Toyoshima, 1993, J. of the Japan Oil Chemist Society, 42(1):30–35.
Tanaka, 1992, JAOCS, 69(12):1210–1214.
Shimada, 1994, JAOCS, 71(9):951–954.
Tanaka, 1994, JAOCS, 71(3):331–334.
Tanaka, 1994, J. Japan Oil Chemists Society, 43(7):39–43.
Lie, 1992, International J. of Food Science and Technology, 27:73–76.

*Primary Examiner*—Carolyn Paden
*Attorney, Agent, or Firm*—Pillsbury Madison & Sutro LLP

[57] ABSTRACT

Fish oil concentrates, having:
 $\geq 40\%$ of long chain poly unsaturated fatty acids
 $<20\%$ of saturated fatty acids ($C_{14}$–$C_{18}$)
 $<15\%$ oleic acid
 $<12\%$ $C_{16:1}$—fatty acid
and with a weight-ratio:
 DHA=0.5–3.0
 EPA
can be obtained by a process involving the following steps
 subjecting a fish oil to an enzymic conversion
 removing free fatty acids or esters from conversion-product
 subjecting product of above to enzymic hydrolysis, using 1.3-specific lipase or partial glyceride-specific lipase
 wash and dry product
 re-esterify dried product

6 Claims, No Drawings

COMPOSITION BASED ON FISH OIL

This is a continuation of application Ser. No. 09/077,200, filed May 26, 1998 now U.S. Pat. No. 6,020,020.

FIELD OF THE INVENTION

The invention relates to fish-oil compositions, procedures for making such compositions and products containing the same.

1. Description of Related Art

Fat-compositions, based on fish oils are well-known in the prior art. Many of these compositions were made and applied, because of the health benefits. E.g. Wo 90/04012 discloses triglycerides, containing saturated $C_8$–$C_{10}$ fatty acid residues in 1.3 and polyunsaturated fatty acid residues in the 2-position. It is stated, that these triglycerides have benificial nutritional properties. According to Wo 94/00044 unhardened fish oils have significant health benefits. Above known oils however have one main, common disadvantage: i.e. either the total level of polyunsaturated fatty acids (such as: EPA, DHA, DPA, etc.) is rather low (i.e.: below 35 wt % in total), or if this level is above 35 wt % its oxidative stability is low, while it also displayed high off-taste. Although it is known in the prior art that the oxidative stability of a triglyceride, containing polyunsaturated fatty acids can be increased by incorporation of saturated fatty residues into the triglycerides, the levels of saturated fatty acids were rather high in order to achieve acceptable stability.

BRIEF SUMMARY OF THE INVENTION

We found new triglycerides, which overcome the drawbacks of the compostions of the prior art. These new compositions combine high levels of polyunsaturated long chain fatty acids, with relatively low levels of saturated fatty acid residues, relatively low off-taste and relatively high oxidative stability. Oxidative stability and off-taste can be evaluated by establishing mean smell scores upon evaluation by a taste-panel. Simultaneously a preference of the panellists can be measured for oils according to the invention, compared with comparative oils. Another method is to measure peroxide values of the different oils. Above triglyceride-compositions can be characterized as fish-oil concentrates, comprising glycerides with:

(i) at least 40 wt %, preferably 40–55 wt %, more preferably 42–52 wt % of w-3 long chain polyunsaturated fatty acids, preferably consisting of two or more of the group consisting of DHA, EPA and DPA (ie: $C_{22:6}$, $C_{20:5}$ and $C_{22:5}$ respectively).

(ii) less than 20 wt %, preferably 2–18 wt %, most preferably 5–15 wt % of total saturated fatty acid with 14–18 C—atoms.

(iii) less than 15 wt %, preferably <12 wt % of $C_{18:1}$— fatty acid.

(iv) less than 12 wt %, preferably <7 wt % of $C_{16:1}$—fatty acid.

(v) while DHA and EPA are present in a weight-ratio of 0.5–3.0, preferably 0.7–2.0.

DETAILED DESCRIPTION OF THE INVENTION

Preferred fish oil concentrates comprise triglycerides and diglycerides in a weight ratio of tri:di>3, preferably 3–50, more preferable 10–35. These concentrates are rich in long chain polyunsaturated fatty acids, whereas its oxidative stability, off-taste and peroxide values are the same or even improved compared with comparative compositions. The SAFA-content of these concentrates is lower than could be expected for above properties.

Although above concentrates could be added perse to foodproducts, it is often better or easier to use a blend with other triglycerides. Therefore our invention also concerns blends of triglycerides comprising:

0.3–95 wt % of the concentrate, and 99.7–5 wt % of a complementary fat, having a solid fat index at 10° C. ($N_{10}$) that is either at least 5% more, or at least 5% less than the $N_{10}$ of the concentrate.

The complementary fat often provides structuring properties to the fatblend. The amounts of complementary fat applied can vary from 98–20 wt %, preferably from 95–60 %. In order to provide structuring characteristics it was found, that the solid fat content (NMR-pulse, not stabilized) of the complementary fat should be >15 at 20° C., preferably ≧20. Very suitable blends are obtained, if the complementary fat is selected from cocoa butter equivalents, cocoa butter, palm oil or fractions thereof, palmkernel oil or fractions thereof, interesterified mixtures of above fats or fractions or hardened components thereof, or from liquid oil, such as sunflower oil, high oleic sunflower oil, fish oil, soybean oil, rapeseed oil, cottonseed oil, safflower oil, high oleic safflower oil, maize oil or MCT oils, hardened liquid oils or fractions thereof or mixtures of one or more of the fats or oils mentioned.

The composition of the blend should preferably be selected in such a way, that the blend displays a solid fat content (NMR-pulse; not stabilized) of 0–85, preferably 10–70, most preferably 20–60 at 5° C. and <30, preferably <20, most preferably <5 at 35° C.

In order to improve the oxygen stability of our triglycerides or blends, containing them, we prefer to add an effective amount of an oxidation stabilizer, selected from the group consisting of: natural or synthetic tocopherols, BHT, BHA, TBHQ, propylgallate, ascorbylester of fatty acids, free radical scavengers, enzymes with anti-oxidant properties.

Our invention further concerns food-products, comprising a fat phase, such as spreads, margarine, cream alternative, infant food, chocolate, confectionery, bakery products, sauces, ice-creams, ice-cream coatings, cheese, soups, mayonnaise, dressings, enteral or parental products, wherein the fat phase contains a concentrate or a blend the present invention.

A very efficient way to dose our new triglycerides, is to make capsules from them. These capsules comprise a filling, encapsulated in an edible coating, wherein the filling consists of the concentrate according to the invention or the blends thereof. In this way our triglycerides can also be eaten, without noticing the disadvantageous off-taste of triglycerides, based on fish-oils.

Our new composition can be made by blending of the individual triglycerides. However, this is not a very economical way. We found a new, more sophisticated process to prepare them, comprising the following steps:

(i) a refined fish oil is subjected to an enzymic hydrolysis or alcoholysis, preferably, using Cand. Rugosa or Geotrichum Candidum (ii) the product of (i) is subjected to a treatment for the removal of free fatty acids or its alkylesters (iii) the product of (ii) is subjected to an enzymic hydrolysis, in particular using a 1,3-selective lipase or a lipase with a specificity for mono- and diglycerides, such as Amono G-lipase (iv) the product of (iii) is washed for the removal of glycerol and dried (v) whereupon the product of (iv) is re-esterified.

In a preferred embodiment the hydrolysis process according to step (i) is performed to a hydrolysis rate of 50–80%. The enzymic treatment according to step (iii) is preferably performed till such a level of free fatty acids, which is at least enough to re-esterify all remaining partial glycerides in the reaction mixture.

Step (v) of above process can be performed as a directed or non-directed enzymic esterification, or as a directed or non-directed chemical esterification, using a base (in particular Na-methanolate) as a catalyst. Directed chemical esterification is performed by removing the triglycerides formed during the conversion, which are insoluble in the reaction solution.

In the most preferred embodiment above process is performed on a fish-oil, having following characteristics:

(a) 10–35 wt % of w-3 long chain, polyunsaturated fatty acids, preferably being DHA, EPA and DPA.

(b) 15–35 wt % of saturated fatty acids with 14–18 C-atoms.

(c) 10–15 wt % of $C_{18:1}$—fatty acid.

(d) 7–15 wt % of $C_{16:1}$—fatty acid.

(e) DHA:EPA—ratio of 0.5–1.5.

EXAMPLES

Example 1

20 kg of refined fish oil, with a fatty acid composition shown in table 1.1, was mixed with 200 ppm of TBHQ antioxidant and 10 kg of 50 mM phosphate buffer pH 7. A suspension of 8 g of *Candida rugosa* lipase in a small quantity of buffer was then added and the mixture stirred vigorously under a nitrogen atmosphere at 25° C. After 26 hours the free fatty acid (FFA) level in the reaction mixture reached 60%. The oil was heated to 90° C. for 10 minutes and the aqueous phase was allowed to settle and drained off. The oil was washed twice with 10 kg degassed/demineralised water and dried at 100° C. under vacuum. The FFA was separated from the partial glycerides by molecular distillation and the fatty acid composition of each fraction is shown in table 1.1. The corresponding glyceride and FFA compositions are shown in table 1.2. 7.7 kg of the partial glyceride fraction obtained as described above was bleached by mixing at 105° C., under vacuum, with 4% of bleaching earth and 0.08% citric acid for 30 minutes followed by filtration. To this oil was added 200 ppm TBHQ antioxidant and an equal amount of degassed/demineralised water followed by 3% immobilised *Rhizomucor miehei* lipase based on the weight of oil. Hydrolysis was carried out by stirring for 3.5 hours at 35° C. The lipase was inactivated by heating the reaction mixture to 90° C. for 15 minutes and the aqueous phase was allowed to settle and drained off with inactivated lipase. The partially hydrolysed oil was washed twice with distilled water and after draining the aqueous phases was dried under vacuum at 100° C. for 0.5.hours. The composition of the resulting oil is shown in table 1.2. After cooling to 55° C., 5% immobilised *Rhizomucor miehei* lipase based on the weight of oil was added and a vacuum of ca. 50 mbar was applied. After 24 hours the diglyceride level had dropped to 2.9% and the reaction was stopped by removing the lipase by filtration. The oil was refined and the fatty acid and glyceride composition of the product is given in table 1.1 and table 1.2 respectively.

TABLE 1.1

| | Fatty acid compositions (wt %) | | | | | | | | |
|---|---|---|---|---|---|---|---|---|---|
| | C14:0 | C16:0 | C16:1 | C16:u | C18:0 | C18:1 | C18:2 | 1C18:3 | C18:4 |
| Fish oil | 6.9 | 18.3 | 7.9 | 5.9 | 3.8 | 13.6 | 1.5 | 0.8 | 2.1 |
| Glyceride fraction | 4.1 | 5.9 | 4.5 | 6.4 | 2.5 | 10.1 | 1.1 | 0.6 | 2.9 |
| FFA fraction | 8.9 | 26.1 | 10.1 | 6.0 | 4.6 | 16.8 | 2.0 | 1.0 | 1.6 |
| Product | 5.3 | 6.1 | 5.0 | 9.3 | 2.3 | 9.2 | 1.5 | 0.6 | 3.6 |
| | C20:0 | C20:1 | C20:5 | C20:u | C22:0 | C22:1 | C22:5 | C22:6 | C22:u |
| Fish oil | 0.2 | 1.6 | 15.9 | 2.3 | 0 | 1.3 | 2.4 | 12.3 | 1.4 |
| Glyceride fraction | 0.3 | 1.8 | 20.2 | 3.4 | 0 | 2.0 | 4.5 | 25.7 | 2.5 |
| FFA fraction | 0.2 | 0.3 | 12.3 | 2.0 | 0 | 0.9 | 0.9 | 2.4 | 1.1 |
| Product | 0.2 | 1.4 | 21.9 | 2.6 | 0.2 | 1.7 | 3.9 | 21.9 | 1.6 |

TABLE 1.2

| | Glyceride and FFA content (wt %). | | | |
|---|---|---|---|---|
| | Triglyceride | Diglyceride | Monoglyceride | FFA |
| Glyceride fraction | 72.6 | 24.6 | 1.3 | 1.5 |
| Partially hydrolysed glyceride fraction | 43.6 | 25.1 | 4.8 | 26.5 |
| Product | 96.8 | 2.9 | 0.1 | 0.1 |

Example 2

A refined fish oil concentrate was made from refined fish oil according to the process described in example 1. The fatty acid composition of the original fish oil and the concentrate is shown in table 2.1. A log sample of each was placed in glass bottles with free exposure to air. The bottles were stored at 50° C. for 1 week, 40° C. for 2 weeks, 20° C. for 3 weeks, 5° C. for 4 weeks. A group of 6 trained panellists evaluated the quality of the samples by smelling the oil at time 0 and after the storage period. Each panellist assigned a score to the sample on a scale of 0 to 6. A score of 0 corresponds to no detectable odour while a score of 6 is an extremely strong odour. The quality of the samples was determined at time 0 and at the end of the storage period. The mean value of the scores of all the panellists is shown in table 2.2. Table 2.3 shows the preferences of the individual panellists for each sample i.e. the number of people who exhibited a preference for one sample over the other, or who found the samples to have the same odour. The samples were also analyzed for peroxide value (PV) as a measure of oxidative deterioration, a higher PV indicating a greater degree of oxidation. The measured PVs at time 0 and after the storage period are shown in table 2.4.

TABLE 2.1

Fatty acid composition of the original fish oil and the concentrate (wt %)

| | C14:0 | C16:0 | C16:1 | C16:u | C18:0 | C18:1 | C18:2 | C18:3 | C18:4 | C20:0 | C20:1 | C20:4 | C20:5 | C20:u | C22:0 | C22:1 | C22:5 | C22:6 | C22:u |
|---|---|---|---|---|---|---|---|---|---|---|---|---|---|---|---|---|---|---|---|
| Fish oil | 6.4 | 15.6 | 8.0 | 5.9 | 3.4 | 15.1 | 1.4 | 1.0 | 2.2 | 0.2 | 1.5 | 1.2 | 16.2 | 1.1 | 0.1 | 1.1 | 2.5 | 13.2 | 1.9 |
| Concentrate | 3.9 | 5.5 | 4.8 | 6.1 | 1.9 | 9.8 | 0.9 | 0.5 | 3.0 | 1.3 | 1.3 | 1.9 | 17.4 | 1.6 | 0.3 | 1.2 | 4.5 | 29.4 | 2.8 |

| | epa + dpa + dha | C14:0 + 16:0 + 18:0 | C18:1 | C16:1 | dha:epa |
|---|---|---|---|---|---|
| Fish oil | 31.9 | 25.4 | 15.1 | 8.0 | 0.8 |
| Concentrate | 51.3 | 11.3 | 9.8 | 4.8 | 1.7 |

TABLE 2.2

Mean smell scores for fish oil and concentrate at time 0 and after storage at different temperatures for different time periods

| Temperature (° C.) | Storage time (weeks) | Mean smell score Fish oil | Mean smell score Concentrate |
|---|---|---|---|
| | 0 | 0.9 | 1 |
| 50 | 1 | 2.9 | 2.9 |
| 40 | 2 | 2.8 | 3.4 |
| 20 | 3 | 2.7 | 2.7 |
| 5 | 4 | 2.3 | 2.1 |

TABLE 2.3

Preferences of individual panellists for fish oil, concentrate or no preference at time 0 and after storage at different temperatures for different time periods

| Temperature (° C.) | Storage time (weeks) | No. of panellists who exhibited a preference for fish oil | none | for concentrate |
|---|---|---|---|---|
| | 0 | 1 | 4 | 1 |
| 50 | 1 | 2 | 2 | 2 |
| 40 | 2 | 4 | 1 | 0 |
| 20 | 3 | 0 | 4 | 1 |
| 5 | 4 | 1 | 3 | 1 |

TABLE 2.4

Peroxide values (PV) for fish oil and concentrate at time 0 and after storage at different temperatures for different time periods

| Temperature (° C.) | Storage time (weeks) | Peroxide Value (PV) Fish oil | Peroxide Value (PV) Concentrate |
|---|---|---|---|
| | 0 | 1.8 | 0.8 |
| 50 | 1 | 13.3 | 8.2 |
| 40 | 2 | 12.2 | 7.6 |
| 20 | 3 | 8.5 | 2.4 |
| 5 | 4 | 3 | 1.2 |

Example 3

A partial glyceride concentrate was prepared from refined fish oil by treatment with C. rugosa lipase according to the process described in example 1. This partial glyceride material was partially hydrolysed using SP392 lipase also as described in example 1. A portion of this material was then reesterified according to the process in example 1. The fatty acid composition and FFA content of the partially hydrolysed material is shown in table 3.1. A log sample of each was placed in glass bottles with free exposure to air. The bottles were stored at 50° C. for 1 week, 40° C. for 2 weeks, 20° C. for 3 weeks, 5° C. for 4 weeks. A group of 6 trained panellists evaluated the quality of the samples by smelling the oil at time 0 and after the storage period. Each panellist assigned a score to the sample on a scale of 0 to 6. A score of 0 corresponds to no detectable odour while a score of 6 is an extremely strong odour. The quality of the samples was determined at time 0 and at the end of the storage period. The mean value of the scores of all the panellists is shown in table 3.2. Table 3.3 shows the preferences of the individual panellists for each sample i.e. the number of people who exhibited a preference for one sample over the other, or who found the samples to have the same odour. The samples were also analyzed for peroxide value (PV) as a measure of oxidative deterioration, a higher PV indicating a greater degree of oxidation. The measured PVs at time 0 and after the storage period are shown in table 3.4.

TABLE 3.1

Fatty acid composition and free fatty acid (FFA) content of the partially hydrolysed concentrate and the reesterified concentrate (wt %)

| | C14:0 | C16:0 | C16:1 | C16:u | C18:0 | C18:1 | C18:2 | C18:3 | C18:4 | C20:0 | C20:1 | C20:4 | C20:5 | C20:u | C22:0 | C22:1 | C22:5 | C22:6 | C22:u |
|---|---|---|---|---|---|---|---|---|---|---|---|---|---|---|---|---|---|---|---|
| Hydrolysed | 3.8 | 5.6 | 4.5 | 6.6 | 1.9 | 9.7 | 1.0 | 0.6 | 3.1 | 1.6 | 1.5 | 1.9 | 17.2 | 1.1 | 0.2 | 1.2 | 4.5 | 30.1 | 2.4 |
| Reesterified | 3.7 | 5.7 | 4.5 | 6.4 | 1.9 | 9.8 | 1.1 | 0.6 | 3.0 | 1.6 | 1.3 | 1.9 | 17.1 | 1.2 | 0.3 | 1.3 | 4.5 | 30.2 | 2.5 |

| | epa + dpa + dha | C14:0 + 16:0 + 18:0 | C18:1 | C16:1 | dha:epa |
|---|---|---|---|---|---|
| Hydrolysed | 51.8 | 11.3 | 9.7 | 4.5 | 1.8 |
| Reesterified | 51.8 | 11.3 | 9.8 | 4.5 | 1.8 |

| | FFA content |
|---|---|
| Hydrolysed | 20.0 |
| Reesterified | 3.9 |

TABLE 3.2 mean smell scores for partially hydrolysed concentrate and reesterified concentrate at time 0 and after storage at different temperatures for different time periods

| | Storage time | Mean smell score | |
|---|---|---|---|
| Temperature (° C.) | (weeks) | Hydrolysed | Reesterified |
| | 0 | 4.4 | 4.5 |
| 50 | 1 | 4.7 | 4.9 |
| 40 | 2 | 4.7 | 4.8 |
| 20 | 3 | 5.8 | 4.9 |
| 5 | 4 | 5.0 | 4.6 |

TABLE 3.3 preferences of individual panellists for partially hydrolysed concentrate, reesterified concentrate or no preference at time 0 and after storage at different temperatures for different time periods

| | | No. of panellists who exhibited a preference | | |
|---|---|---|---|---|
| Temperature (° C.) | Storage time (weeks) | for hydrolysed | none | for reesterified |
| | 0 | 2 | 3 | 1 |
| 50 | 1 | 1 | 4 | 1 |
| 40 | 2 | 2 | 3 | 0 |
| 20 | 3 | 0 | 1 | 5 |
| 5 | 4 | 0 | 1 | 4 |

TABLE 3.4

Peroxide values (PV) for partially hydrolysed concentrate and reesterified concentrate at time 0 and after storage at different temperatures for different time periods

| | Storage time | Peroxide Value (PV) | |
|---|---|---|---|
| Temperature (° C.) | (weeks) | Hydrolysed | Reesterified |
| | 0 | 2.9 | 2.1 |
| 50 | 1 | 1.5 | 4.5 |
| 40 | 2 | 1.4 | 5.1 |
| 20 | 3 | 5.6 | 5.6 |
| 5 | 4 | 5.9 | 3.7 |

Example 4

A refined fish oil concentrate was prepared from refined fish oil according to the process described in example 1. A high saturates concentrate was prepared by dissolving 2 parts of Dynasan (fully hardened soybean oil) in 9 parts of the fish oil concentrate at 80° C. for 15 minutes. The concentrate without Dynasan was also heated at 80° C. for 15 minutes. Upon cooling to room temperature, the concentrate was liquid and completely clear but the high saturates concentrate formed a opaque solid. The fatty acid composition of the concentrate and the high saturates concentrate is shown in table 4.1. A log sample of each was placed in glass bottles with free exposure to air. The bottles were stored at 50° C. for 1 week, 40° C. for 2 weeks, 20° C. for 3 weeks, 5° C. for 4 weeks. A group of 6 trained panellists evaluated the quality of the samples by smelling the oil at time 0 and after the storage period. Each panellist assigned a score to the sample on a scale of 0 to 6. A score of 0 corresponds to no detectable odour while a score of 6 is an extremely strong odour. The quality of the samples was determined at time 0 and at the end of the storage period. The mean value of the scores of all the panellists is shown in table 4.2. Table 4.3 shows the preferences of the individual panellists for each sample i.e. the number of people who exhibited a preference for one sample over the other, or who found the samples to have the same odour. The samples were also analyzed for peroxide value (PV) as a measure of oxidative deterioration, a higher PV indicating a greater degree of oxidation. The measured PVs at time 0 and after the storage period are shown in table 4.4.

TABLE 4.1

Fatty acid composition of the concentrate and the high saturates concentrate (wt %)

| | C14:0 | C16:0 | C16:1 | C16:u | C18:0 | C18:1 | C18:2 | C18:3 | C18:4 | C20:0 | C20:1 | C20:4 | C20:5 | C20:u | C22:0 | C22:1 | C22:5 | C22:6 | C22:u |
|---|---|---|---|---|---|---|---|---|---|---|---|---|---|---|---|---|---|---|---|
| Concentrate | 3.9 | 5.5 | 4.8 | 6.1 | 1.9 | 9.8 | 0.9 | 0.5 | 3.0 | 1.3 | 1.3 | 1.9 | 17.4 | 1.6 | 0.3 | 1.2 | 4.5 | 29.4 | 1.9 |
| High Sats | 3.4 | 4.7 | 4.4 | 4.6 | 21.4 | 8.1 | 0.8 | 0.4 | 2.4 | 0.2 | 1.2 | 1.7 | 14.0 | 0.6 | 0.0 | 1.3 | 3.5 | 23.3 | 2.0 |

| | epa + dpa + dha | C14:0 + 16:0 + 18:0 | C18:1 | C16:1 | dha:epa |
|---|---|---|---|---|---|
| Concentrate | 51.3 | 11.3 | 9.8 | 4.8 | 1.7 |
| High Sats | 40.8 | 29.5 | 8.1 | 4.4 | 1.7 |

TABLE 4.2

Mean smell scores for concentrate and high saturates concentrate at time 0 and after storage at different temperatures for different time periods

| | | Mean smell score | |
|---|---|---|---|
| Temperature (° C.) | Storage time (weeks) | Concentrate | High saturates concentrate |
| | 0 | 1.6 | 1.6 |
| 50 | 1 | 2.9 | 2.5 |
| 40 | 2 | 2.9 | 2.9 |
| 20 | 3 | 2.7 | 2.9 |
| 5 | 4 | 2.3 | 2.3 |

TABLE 4.3

Preferences of individual panellists for concentrate and high saturated concentrate at time 0 and after storage at different temperatures for different time periods

| | | No. of panellists who exhibited a preference | | |
|---|---|---|---|---|
| Temperature (° C.) | Storage time (weeks) | for concentrate | none | for high saturates concentrate |
| | 0 | 1 | 2 | 3 |
| 50 | 1 | 1 | 1 | 4 |
| 40 | 2 | 1 | 3 | 1 |
| 20 | 3 | 1 | 4 | 0 |
| 5 | 4 | 1 | 3 | 1 |

TABLE 4.4

Peroxide values (PV) for concentrate and high saturates concentrate at time 0 and after storage at different temperatures for different time periods

| | | Peroxide Value (PV) | |
|---|---|---|---|
| Temperature (° C.) | Storage time (weeks) | Concentrate | High saturates concentrate |
| | 0 | 1.1 | 1.2 |
| 50 | 1 | 8.6 | 3.9 |
| 40 | 2 | 9.9 | 4.3 |
| 20 | 3 | 3 | 3.2 |
| 5 | 4 | 1.5 | 1.9 |

What is claimed is:

1. A fish-oil concentrate comprising glycerides with:
   (i) at least 40 wt % of w-3 long chain polyunsaturated fatty acids, comprising at least DHA and EPA (ie: $C_{22:6}$ and $C_{20:5}$ respectively),
   (ii) less than 20 wt % of total saturated fatty acid with 14–18 C—atoms,
   (iii) less than 15 wt % of $C_{18:1}$-fatty acid,
   (iv) less than 12 wt % of $C_{16:1}$-fatty acid, and
   (v) the weight ratio of DHA to EPA being in the range 0.05–3.0.

2. A fish oil concentrate, according to claim 21, wherein the concentrate comprises triglycerides and diglycercides in a weight-ratio of >3.

3. A fish oil concentrate according to claim 2 wherein the weight-ratio of triglycerides and diglycerides is in the range 10–35.

4. A food product comprising a fat phase selected from the group consisting of spreads, margarine, cream alternative, infant food, chocolate, confectionery, bakery products, sauces, ice-creams, ice-cream coatings, cheese, soups, mayonnaise, dressings, enteral or parental products, wherein the fat phase contains a concentrate according to claim 1.

5. A capsule which comprises a filling, encapsulate d in an edible coating, wherein the filling consists of the concentrate according to claim 1 or 2.

6. A fish oil concentrate according to claim 1 comprising 42–52 wt % of (i) and said component (i) includes DPA (ie: $C_{22:5}$);
   5–15 wt % of (ii);
   <12 wt % of (iii);
   <7 wt % of (iv); and
   the weight ratio of DHA and EPA is 0.7–2.0.

* * * * *